US010147223B2

United States Patent
Kim et al.

(10) Patent No.: US 10,147,223 B2
(45) Date of Patent: Dec. 4, 2018

(54) APPARATUS AND METHOD FOR COMPUTER-AIDED DIAGNOSIS

(71) Applicant: Samsung Electronics Co., Ltd., Suwon-si, Gyeonggi-do (KR)

(72) Inventors: Ye-Hoon Kim, Seoul (KR); Moon-Ho Park, Hwaseong-si (KR); Yeong-Kyeong Seong, Yongin-si (KR); Jung-Hoe Kim, Seongnam-si (KR); Baek-Hwan Cho, Seoul (KR)

(73) Assignee: Samsung Electronics Co., Ltd., sUWON-SI (KR)

( * ) Notice: Subject to any disclaimer, the term of this patent is extended or adjusted under 35 U.S.C. 154(b) by 0 days.

(21) Appl. No.: 15/477,771

(22) Filed: Apr. 3, 2017

(65) Prior Publication Data

US 2017/0206699 A1 Jul. 20, 2017

Related U.S. Application Data

(63) Continuation of application No. 14/469,854, filed on Aug. 27, 2014, now Pat. No. 9,639,929.

(30) Foreign Application Priority Data

Oct. 24, 2013 (KR) .................. 10-2013-0127246

(51) Int. Cl.
*G06K 9/00* (2006.01)
*G06T 7/00* (2017.01)
(Continued)

(52) U.S. Cl.
CPC .......... *G06T 15/005* (2013.01); *A61B 5/0033* (2013.01); *G01R 33/4814* (2013.01);
(Continued)

(58) Field of Classification Search
CPC ..... G06T 15/005; G06T 7/0012; G06T 15/08; G06T 19/003; G06T 2200/04;
(Continued)

(56) References Cited

U.S. PATENT DOCUMENTS 8,083,680 B2  12/2011  Choi
2005/0102315 A1  5/2005  Krishnan
(Continued)

FOREIGN PATENT DOCUMENTS

CN  1836240 A  9/2006
CN  101517614 A  8/2009
(Continued)

OTHER PUBLICATIONS

Kawata et al. "Classification of Pulmonary Nodules in Thin-section CT Images Based on Shape Characterization." Proceedings, International Conference on Image Processing, Oct. 26, 1997, pp. 528-530.*

(Continued)

*Primary Examiner* — Jon Chang
(74) *Attorney, Agent, or Firm* — Jefferson IP Law, LLP

(57) ABSTRACT

An apparatus and method for medical diagnostics includes receiving three-dimensional (3D) volume data of a part of a patient's body, and generating two-dimensional (2D) slices including cross-sections of the 3D volume data cut from a cross-section cutting direction. The apparatus and the method also determine whether a lesion in each of the 2D slices is benign or malignant and output results indicative thereof, select a number of the 2D slices based on the results, and make a final determination whether the lesion is benign or malignant based on the selected 2D slices.

20 Claims, 17 Drawing Sheets

(51) Int. Cl.
  *G06T 15/08* (2011.01)
  *G06T 19/00* (2011.01)
  *A61B 5/00* (2006.01)
  *G01R 33/48* (2006.01)
  *G06T 15/00* (2011.01)

(52) U.S. Cl.
  CPC ........ *G06K 9/00536* (2013.01); *G06T 7/0012* (2013.01); *G06T 15/08* (2013.01); *G06T 19/003* (2013.01); *G06T 2200/04* (2013.01); *G06T 2200/08* (2013.01); *G06T 2207/10072* (2013.01); *G06T 2207/10088* (2013.01); *G06T 2207/10136* (2013.01)

(58) Field of Classification Search
  CPC ....... G06T 2200/08; G06T 2207/10072; G06T 2207/10088; G06T 2207/10136; G06T 2207/30096; G06T 2207/10081; G06K 9/00536; G01R 33/4814; A61B 5/0033; A61B 6/02
  See application file for complete search history.

(56) References Cited

U.S. PATENT DOCUMENTS

| | | |
|---|---|---|
| 2005/0232474 A1 | 10/2005 | Wei et al. |
| 2008/0025592 A1 | 1/2008 | Jerebko et al. |
| 2009/0003676 A1 | 1/2009 | Li |
| 2009/0034684 A1 | 2/2009 | Bernard et al. |
| 2010/0076921 A1* | 3/2010 | Kato ............... G06F 19/321 706/52 |
| 2010/0104154 A1 | 4/2010 | Chan et al. |
| 2011/0087094 A1 | 4/2011 | Ohuchi et al. |
| 2012/0189178 A1 | 7/2012 | Seong |
| 2013/0012820 A1 | 1/2013 | Brown et al. |
| 2013/0016092 A1 | 1/2013 | Collins et al. |
| 2013/0202173 A1 | 8/2013 | Buckler et al. |
| 2015/0196281 A1* | 7/2015 | Takagi ............... A61B 8/06 600/408 |

FOREIGN PATENT DOCUMENTS

| | | | | |
|---|---|---|---|---|
| CN | 102429679 A | | 5/2012 | |
| EP | 2 584 528 A2 | | 4/2013 | |
| JP | 2012045225 A | | 3/2012 | |
| KR | 10-2008-0085420 A | | 9/2008 | |
| WO | 2008035286 A2 | | 3/2008 | |
| WO | WO 2009105530 A2 * | | 8/2009 | ............ G01R 33/56 |
| WO | 2011044295 A2 | | 4/2011 | |

OTHER PUBLICATIONS

Extended European Search Report dated Mar. 25, 2015 in European Application No. 14190030.8 (7 pages).

"3D Ultrasonic Diagnosis of Breast Tumors", Wei-Ming Chen, pp. 1-77.

Xu, Ye, et aL "Comparison of image features calculated in different dimensions for computeraided diagnosis of lung nodules." SPIE Medical Imaging. vol. 7260, 2009.

Huo, Jing. et al. "Sampling-based ensemble segmentation against inter-operator variablity." SPIE Medical imaging. vol. 7963, 2011.

Zhou, Xiangrong, et al. "Automatic localization of solid organs on 3D CT images by a collaborative majority voting decision based on ensemble learning." Computerized Medical Imaging and Graphics vol. 36, 2012: 304-313.

Elizabeth et al."Computer-aided diagnosis of lung cancer on analysis of the significant slice of chest computed tomography image". IET image Processing, vol. 6, issue 6, Aug. 2012, pp. 697-705.

Chinese Office Action dated Sep. 27, 2018, issued in Sipo in connection with a counterpart Chinese application No. 201410553569.0.

* cited by examiner

N: TOTAL NUMBER OF CROSS-SECTIONS

APPARATUS AND METHOD FOR
COMPUTER-AIDED DIAGNOSIS

CROSS-REFERENCE TO RELATED
APPLICATION(S)

This application is a continuation application of prior application Ser. No. 14/469,854, filed on Aug. 27, 2014, now U.S. Pat. No. 9,639,929, issued May 2, 2017 which claims the benefit under 35 U.S.C. § 119(a) of Korean Patent Application No. 10-2013-0127246, filed on Oct. 24, 2013, in the Korean Intellectual Property Office, the entire disclosures of each of which is incorporated herein by references for all purposes.

BACKGROUND

Field

The following description relates to a method and apparatus for medical diagnostics using Computer-Aided Diagnosis (CAD).

Description of the Related Art

Computer Aided Diagnosis (CAD) is a system used to create, modify, analyze, or optimize an image design. CAD supports the analyses of medical images of a part of a patient's body and diagnoses of a lesion from each medical image, which are produced to assist a doctor in making an accurate diagnosis. Recently, rapid developments in medical equipment has prompted introduction of medical devices that process and output three-dimensional (3D) images representing inner cross-sections of parts of a patient's body. In addition, many attempts have been made to develop CAD technologies using 3D images.

A 3D image is an image representing a part of a patient's body in a three-dimensional manner. However, the 3D image does not provide great visibility of organs or tissues within volume data. In addition, despite enormous efforts made to develop CAD techniques using 3D images, when making diagnoses, doctors and other medical experts still depend on and are more comfortable with using two-dimensional (2D) medical images, rather than 3D images.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an illustrative configuration, there is provided a method for medical diagnostics, including receiving three-dimensional (3D) volume data of a part of a patient's body; generating two-dimensional (2D) slices including cross-sections of the 3D volume data cut from a cross-section cutting direction; determining whether a lesion in each of the 2D slices is benign or malignant and outputting results indicative thereof; selecting a number of the 2D slices based on the results; and making a final determination whether the lesion is benign or malignant based on the selected 2D slices.

The determining may include applying each of the 2D slices to a diagnostic model to determine whether the lesion in each of the 2D slices is benign or malignant.

The determining may include applying each of the 2D slices to a single diagnostic model that is generated based on a cross-section cutting direction to determine whether the lesion in each of the 2D slices is benign or malignant.

The determining may include applying the 2D slices to respective diagnostic models that are generated based on cross-section cutting directions of the 2D slices to determine whether the lesion in each of the 2D slices is benign or malignant.

Each of the results may include a classification result of the lesion in each of the 2D slices as either benign or malignant, and a confidence level of the classification result.

The generating of the 2D slices may include generating a virtual plane, and generating the 2D slices including cross-sections of the 3D volume data cut by the virtual plane.

The generating of the virtual plane may include generating the virtual plane by changing coefficient values of a plane equation that represents an arbitrary plane of the 3D volume data.

The generating of the at least one virtual plane may include generating the at least one virtual plane by performing principal component analysis (PCA) on the 3D volume data.

The generating of the virtual plane may include determining feature points having a predetermined feature from among voxels of the 3D volume data based on values of the voxels, and generating the virtual plane based on a distribution of the feature points by performing the PCA.

The generating of the virtual plane may include calculating a first principal component vector corresponding to an axis in a direction in which a change in the 3D volume data is the greatest by performing the PCA, and generating the virtual plane with reference to the first principal component vector.

The generating of the virtual plane may include detecting a mass included in the 3D volume data based on values of voxels of the 3D volume data; and generating the virtual plane based on a distribution of points included in the mass by performing the PCA.

The generating of the virtual plane may include generating the virtual plane based on a user's input information.

In accordance with another illustrative configuration, there is provided an apparatus for medical diagnostics, including a receiver configured to receive three-dimensional (3D) volume data of a part of a patient's body; an image processor configured to generate two-dimensional (2D) slices including cross-sections of the 3D volume data cut from a cross-section cutting direction; a first diagnoser configured to determine whether a lesion in each of the 2D slices is benign or malignant and to output results indicative thereof; a selector configured to select a number of the 2D slices based on the results; and a second diagnoser configured to determine whether the lesion is benign or malignant based on the selected 2D slices.

The first diagnoser may determine whether the lesion in each of the 2D slices is benign or malignant by applying the 2D slices to a single diagnostic model.

The first diagnoser may determine whether the lesion in each of the 2D slices is benign or malignant by applying the 2D slices to a single diagnostic model generated based on a cross-section cutting direction.

The first diagnoser may determine whether the lesion in each of the 2D slices is benign or malignant by applying the 2D slices to respective diagnostic models generated based on cross-section cutting directions of the 2D slices.

Each of the results may include a classification result of the lesion in each of the 2D slices as either benign or malignant and a confidence level of the classification result.

The image processor may be further configured to include a virtual plane generator configured to generate a virtual plane, and a 2D slice generator configured to generate 2D slices of cross-sections of the 3D volume data cut by the virtual plane.

The virtual plane generator may be further configured to generate the virtual plane by changing coefficients of a plane equation of an arbitrary plane of the 3D volume data.

The virtual plane generator may be further configured to generate the virtual plane by performing principal component analysis (PCA) on the 3D volume data.

The virtual plane generator may be further configured to determine feature points with a predetermined feature from among voxels of the 3D volume data based on values of the voxels, and generate the virtual plane based on a distribution of the feature points.

The virtual plane generator may be further configured to calculate a first principal component vector corresponding to an axis in a direction toward which a greatest change occurs in the 3D volume data by performing the PCA, and generate the virtual plane based on the first principal component vector.

The virtual plane generator may be further configured to detect a mass included in the 3D volume data based on values of voxels of the 3D volume data, and generate the virtual plane based on a distribution of points included in the mass by performing the PCA.

The virtual plane generator may be further configured to generate the virtual plane based on a user's input information.

The second diagnoser may be configured to determine whether the lesion is benign or malignant based on a classification result of the lesion in each of the selected 2D slices.

The first diagnoser may be configured to generate a feature vector using extracted features of a lesion and apply the feature vector to a diagnostic model to classify the lesion as either benign or malignant and to calculate a confidence level of the classification result.

The selector may bind two or more 2D slices into one group, compare confidence levels of the 2D slices in the group, and select one or more 2D slices in descending order of the confidence levels thereof.

The selector may randomly bind the selected 2D slices into one group, compare confidence levels thereof, and select one or more 2D slices in descending order of the confidence levels thereof.

In accordance with an illustrative configuration, there is provided a method for medical diagnostics, including receiving three-dimensional (3D) volume data of a part of a patient's body; generating two-dimensional (2D) slices that represent cross-sections of the 3D volume data cut from a cross-section cutting direction; generating an integrated diagnostic model including a combination of diagnostic models corresponding to cross-section cutting directions of the 2D slices; and determining whether a lesion in each of the 2D slices is benign or malignant by applying at least one of the 2D slices to the integrated diagnostic model.

The generating of the integrated diagnostic model may include selecting, from among the diagnostic models, at least one diagnostic model generated based on cross-section cutting directions that are identical to cross-section cutting directions of the 2D slices; and generating the integrated diagnostic model by integrating the at least one selected diagnostic model.

The generating of the 2D slices may include generating a virtual plane, and generating the 2D slices that represent cross-sections of the 3D volume data cut by the virtual plane.

The generating of the virtual plane may include generating the virtual plane by changing coefficients of a plane equation that represents an arbitrary plane in the 3D volume data.

The generating of the virtual plane may include generating the virtual plane by performing principal component analysis (PCA) on the 3D volume data.

In accordance with another illustrative configuration, there is provided an apparatus for medical diagnostics, including a receiver configured to receive three-dimensional (3D) volume data of a part of a patient's body; an image processor configured to generate two-dimensional (2D) slices including cross-sections of the 3D volume data cut in a cross-section cutting direction; and a diagnoser configured to generate an integrated diagnostic model including a combination of diagnostic models corresponding to cross-section cutting directions of the 2D slices, and to determine whether a lesion in each of the 2D slices is benign or malignant by applying at least one of the 2D slices to the integrated diagnostic model.

The diagnostic models may be generated based on cross-section cutting directions that are identical to cross-section cutting directions of the 2D slices.

The image processor may be configured to include a virtual plane generator configured to generate a virtual plane, and a 2D slice generator configured to generate the 2D slices that represent cross-sections of 3D volume data cut by the virtual plane.

The virtual plane generator may be further configured to generate the virtual plane by changing coefficients of a plane equation that represents an arbitrary plane in the 3D volume data.

The virtual plane generator may be further configured to generate the virtual plane by performing principal component analysis (PCA) on the 3D volume data.

The image processor may be further configured to perform a principal component analysis (PCA) on the 3D volume data to calculate a first principal component vector corresponding to an axis in a direction in which a first greatest change occurs in the 3D volume data and to calculate a second principal component vector indicating an axis in a direction in which a second greatest change occurs in the 3D volume data, and configured to calculate a virtual plane including the first principal component vector and the second principal component vector.

The image processor may further include a virtual plane generator configured to calculate a virtual plane having a greatest change of the 3D volume data, and generate an additional virtual plane in parallel with the virtual plane, and a two-dimensional (2D) slice generator configured to extract voxels intersecting the virtual plane among all voxels in the 3D volume data, and generate each 2D slice by displaying values of the extracted voxels as values of pixels on the virtual plane.

Other features and aspects may be apparent from the following detailed description, the drawings, and the claims.

BRIEF DESCRIPTION OF THE DRAWINGS

These and/or other aspects will become apparent and more readily appreciated from the following description of the embodiments, taken in conjunction with the accompanying drawings in which.

Figure 1:
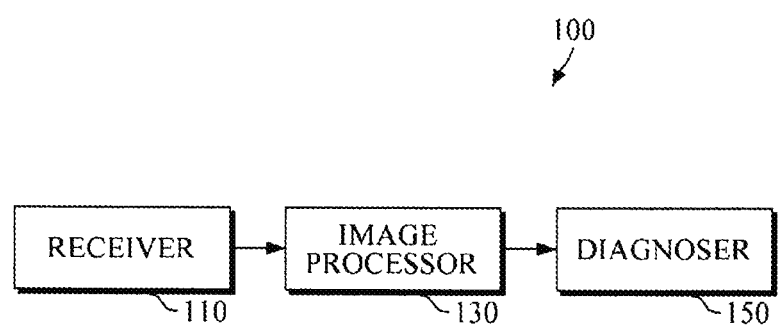
FIG. 1 is a configuration diagram illustrating an apparatus for medical diagnostics using Computer-Aided Diagnosis (CAD), according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, embodiments are described in detail with reference to accompanying drawings.

FIG. 1 is a configuration diagram illustrating an apparatus for medical diagnostics using Computer Aided Diagnosis (CAD), according to an embodiment.

Referring to FIG. 1, an apparatus for CAD 100 includes a receiver 110, an image processor 130, and a diagnoser 150. The receiver 110, the image processor 130, and the diagnoser 150 are structural elements.

The receiver 110 receives volume data representing a part of a patient's body in a three-dimensional (3D) manner, and transmits the received volume data to the image processor 130. The volume data may be acquired from a three dimensional medical image acquisition device, such as a 3D ultrasound image device using 3D probe, Computed Tomography (CT), Magnetic Resonance Imaging (MRI), or an X-ray capturing device.

For example, in the case of ultrasound images, cross-sectional images of a specific part of a patient's body are generated by changing a location and direction of an ultrasound probe placed over the patient's body. The generated cross-sectional images are accumulated to generate volume data representing the specific part of the patient's body in 3D. As such, a method to generate the volume data by accumulating cross-sectional images is called Multiplanar Reconstruction (MPR).

Figure 2:
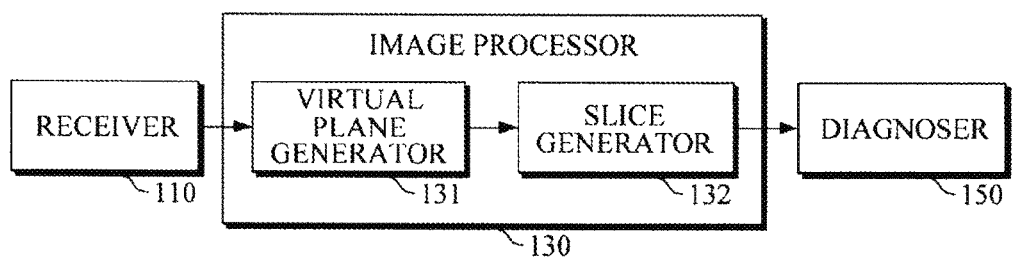
FIG. 2 is a configuration diagram illustrating an image processor, according to an embodiment.

The image processor 130 generates two-dimensional (2D) slices including cross-sections of the volume data received through the receiver 110. The volume data is cut from at least one direction to generate the 2D slices. The image processor 130 transmits the 2D slices to the diagnoser 150. In one example, the image processor 130 generates at least one virtual plane in 3D space of the volume data, and then generates the 2D slices including cross-sections of the volume data cut through the generated virtual plane. Referring to FIG. 2, the image processor 130 includes a virtual plane generator 131 and a 2D slice generator 132.

The virtual plane generator 131 generates at least one virtual plane using a full search or principal component analysis (PCA).

The virtual plane generator 131 changes an inclination value and centric coordinates of an arbitrary plane equation to generate all virtual planes of the volume data, which are generated in 3D space (full search).

For instance, the virtual plane generator 131 generates a virtual plane using a plane equation like the following Equation 1.

$$(i-i_d)+p_d(j-j_d)+q_d(k-k_d)=0 \qquad \text{[Equation 1]}$$

Equation 1 is a plane equation that passes through coordinates (id, jd, kd) in 3D space of the volume data and is perpendicular to a vector (1, pd, qd). By changing inclination values pd, qd and centric coordinates id, jd, kd, the virtual plane generator 131 generates a plane equation of each virtual plane of the volume data that is generated in 3D space.

Figure 4A:
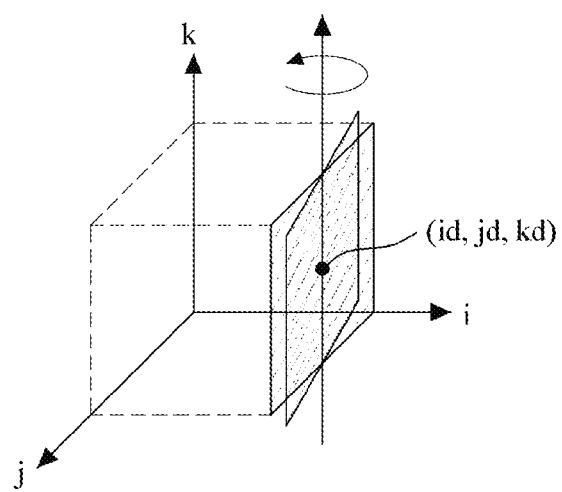
FIGS. 4A-4C is an example of a full search.
Figure 4B:
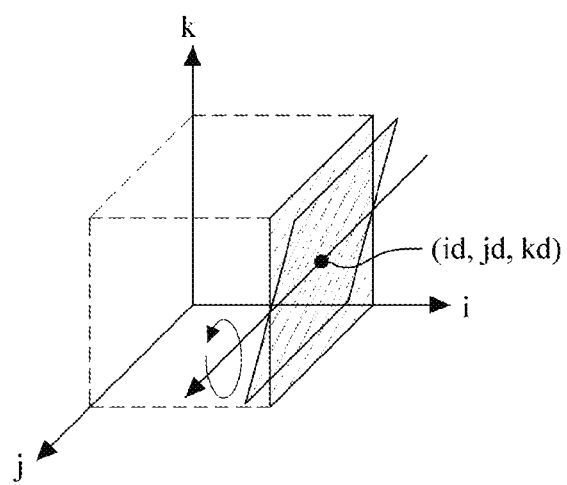
Figure 4C:
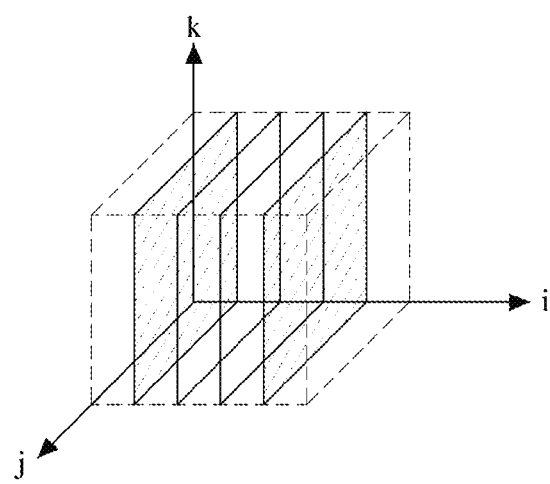

FIG. 4A-4C illustrate an example of determining a cross-section cutting direction by performing a full search. FIG. 4A demonstrates planes of the volume data which rotate within a range between −90° and 90° around a vector being perpendicular to a plane ij and passing through a point (id, jd, kd) in 3D space. FIG. 4A illustrates the planes of the volume data when an inclination value pd is changed, while other coefficients of Equation 1 are fixed.

FIG. 4B demonstrates planes which rotates within a range between −90° and 90° around a vector being perpendicular to a plane ik and passing through a point (id, jd, kd) in 3D space. In this example, an inclination value qd is changed with other coefficients of Equation 1 being fixed.

FIG. 4C demonstrates planes which include a point (id, jd, kd) in 3D space, when an inclination value id is changed while other coefficients of Equation 1 are fixed.

Even in the case where the other coefficients jd and kd of the centric coordinates are changed, it is possible to generate planes including a point (id, jd, kd) in the 3D space in a similar way of generating planes as illustrated in FIG. 4C.

In another example, the virtual plane generator 131 generates at least one virtual plane by performing principal component analysis (PCA) of the received volume data.

For instance, the virtual plane generator 131 calculates a first principal component vector corresponding to an axis in a direction in which a greatest change occurs in the volume data in 3D space by performing the PCA on the volume data. The virtual plane generator 131 then generates at least one virtual plane based on the first principal component vector. For example, when a first principal component vector and a second principal component vector are determined through PCA of the volume data, the virtual plane generator 131 calculates a virtual plane including the first principal component vector and the second principal component vector. The second principal component vector indicates an axis in a direction in which a second greatest change occurs in the volume data in the 3D space. Because principal component vectors indicate axes in respective directions in the 3D space, a single plane may be defined by two of the principal component vectors. This plane corresponds to a plane having the greatest change in the volume data according to the PCA.

Because the PCA is a statistical analysis method, the PCA may not provide completely accurate results. Therefore, the virtual plane generator 131 further calculates additional principal component vectors, in addition to the first and second principal component vectors, and then generates a plurality of planes based on a set of three or more additional principal component vectors in a method to generate at least one virtual plane.

Hereinafter, an example of determining a cross-section cutting direction by performing PCA is described with reference to FIGS. 5A-5B and 6A-6C.

Figure 5A:
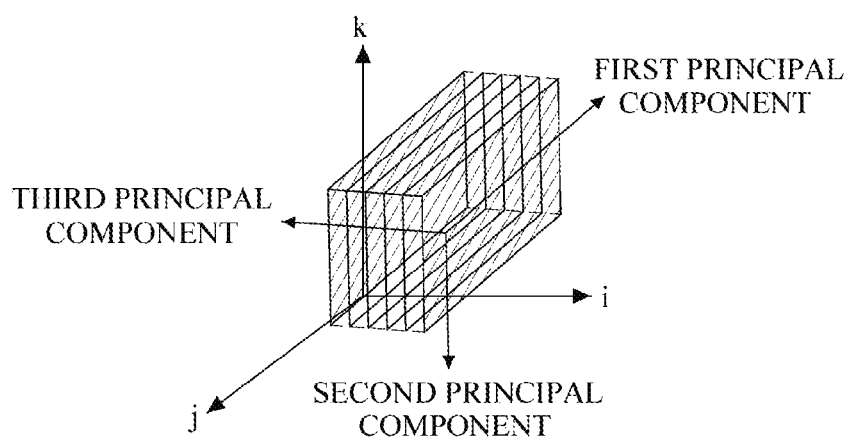
FIGS. 5A-5B and 6A-6C are examples of principal component analysis (PCA)
Figure 5B:
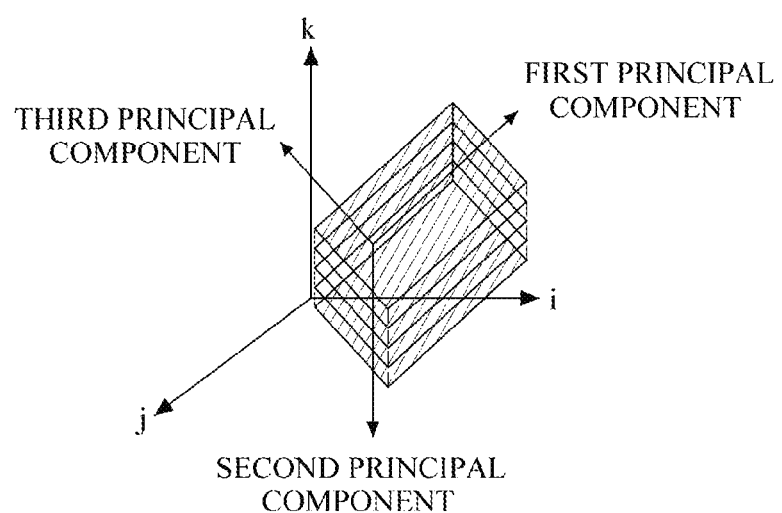

The front plane among all the planes illustrated in FIG. 5A is a plane including first and second principal component vectors. The remaining planes in FIG. 5A are planes that are generated by parallelly moving the plane, including the first principal component vector and the second principal component vector, in a direction of the third principal component vector. The front plane among all the planes illustrated in FIG. 5B is a plane including first and third principal component vectors. The remaining planes in FIG. 5B are planes that are generated by parallelly moving the plane, including the first principal component vector and the third principal component vector, in a direction of the second principal component vector.

Furthermore, the virtual plane generator 131 generates at least one virtual plane according to a change pattern of the volume data in 3D space by performing 2D PCA on the volume data. For instance, the virtual plane generator 131 performs 2D PCA on received volume data to calculate a virtual plane having a greatest change of the received volume data in 3D space, and generates at least one virtual plane based on the calculated virtual plane. In addition, the virtual plane generator 131 generates an additional virtual plane by moving the previously generated virtual plane in parallel, so that the additionally generated virtual plane is in parallel with the previously generated virtual plane.

Figure 6A:
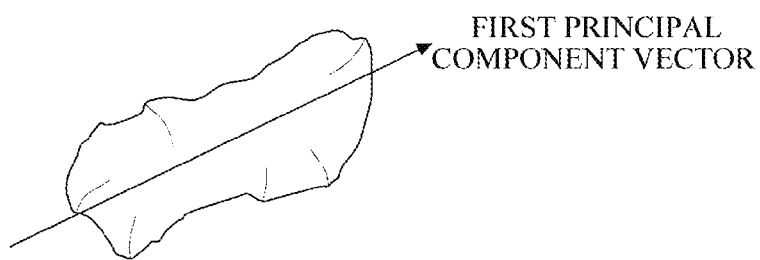

Referring to FIG. 6A, the virtual plane generator 131 detects a mass included in the volume data based on voxel values of the volume data, and calculates a principal component vector from a distribution of points included in the mass in a 3D space. The mass is an object included in the volume data. When the volume data includes a mass, voxel values may be significantly changed in a boundary of the mass. However, anatomical tissues are not homogeneous, and boundaries of the anatomical tissues are not clearly defined in an image in most cases. In addition, information regarding a form or an image characteristic of a predetermined tissue that a medical expert desires to diagnose may be necessary.

There are various methods of segmenting a mass in volume data, such as a level set method. The level set method (LSM) is a numerical technique for tracking interfaces and shapes. One of the many advantages of the level set method is that one can perform numerical computations involving curves and surfaces on a fixed Cartesian grid without having to parameterize these objects. Also, the level set method makes enables to follow shapes that change topology, for example when a shape splits in two, develops holes, or the reverse of these operations. For example, the virtual plane generator 131 segments the mass in volume data based on voxel values of the volume data using the level set method.

Figure 6B:
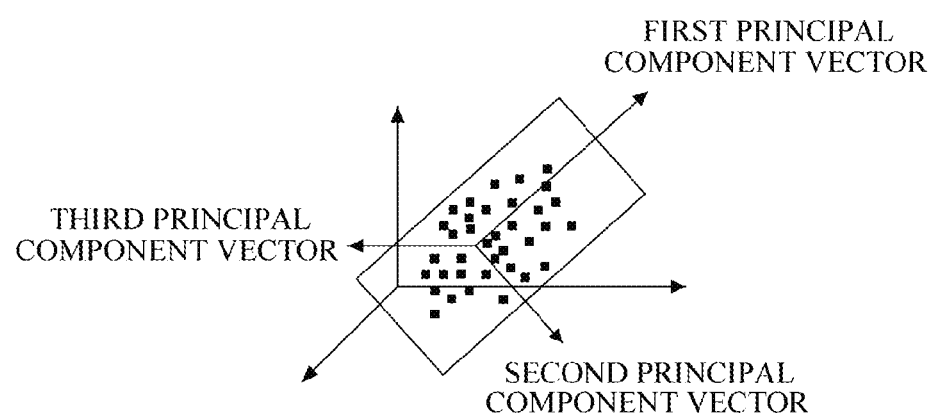

Referring to FIG. 6B, the virtual plane generator 131 identifies feature points, including a feature, such as a form or an image characteristic of a predetermined tissue from among the voxels of the volume data based on the values of the voxels. The virtual plane generator 131 calculates a principal component vector from a distribution of the identified points in a 3D space.

Figure 6C:
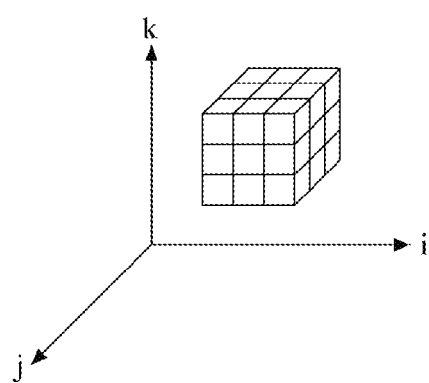

Referring to FIG. 6C, the virtual plane generator 131 calculates a feature of any one of the voxels of the volume data using a voxel set having a predetermined size. A voxel is located at the center of the voxel set. In one example, the virtual plane generator 131 determines a mean brightness value of voxels forming the voxel set as a feature of the center voxel of the voxel set. In another example, the virtual plane generator 131 determines a variance of brightness values of voxels forming the voxel set as the feature of the center voxel of the voxel set.

Also, a method in which the virtual plane generator 131 generates a virtual plane is not limited to the above-described examples, and other various methods may be applied. For example, the virtual plane generator 131 generates at least one virtual plane based on a user's input information. The virtual plane generator 131 generates at least one virtual plane with reference to a cutting direction input by a user through a user interface.

The two-dimensional (2D) slice generator 132 generates 2D slices including cross sections of volume data cut from the virtual plane generated at the virtual plane generator 131. For instance, the 2D slice generator 132 extracts voxels intersecting the virtual plane generated at the virtual plane generator 131 among all the voxels in the volume data. Then, the 2D slice generator 132 generates each 2D slice by displaying values of the extracted voxels as values of pixels on the virtual plane.

An image having a resolution sufficient for a medical practitioner to perform diagnosis may not be provided using only the voxels crossed by the virtual plane generated at the virtual plane generator 131 from among the voxels of the volume data. Accordingly, in order to improve the resolution sufficient for a medical practitioner to perform diagnosis using the values of the voxels of the volume data, the 2D slice generator 132 interpolates additional pixels of a 2D image other than the pixels of the 2D image corresponding to the extracted voxels. The 2D slice generator 132 generates a single 2D image by merging values of the pixels of the 2D image corresponding to the extracted voxels and the interpolated values of the additional pixels of the 2D image. In this manner, an image having a resolution sufficient for a medical expert to perform a diagnosis is generated through this interpolation.

The diagnoser 150 performs diagnosis on each of the 2D slices generated at the 2D slice generator 110. The diagnoser 150 is a structural processor, machine, or a structural intelligent central element configured to make a determination as to whether a lesion in each of the 2D slices is benign or malignant. The determination may include a classification result of a lesion as either benign or malignant, and a confidence level of the classification result. The diagnoser 150 may select some of the 2D slices based on results of the determination, and then make a final determination as to whether a lesion in the volume data is benign or malignant based on results of determination relative to the selected 2D slices.

Figure 3:
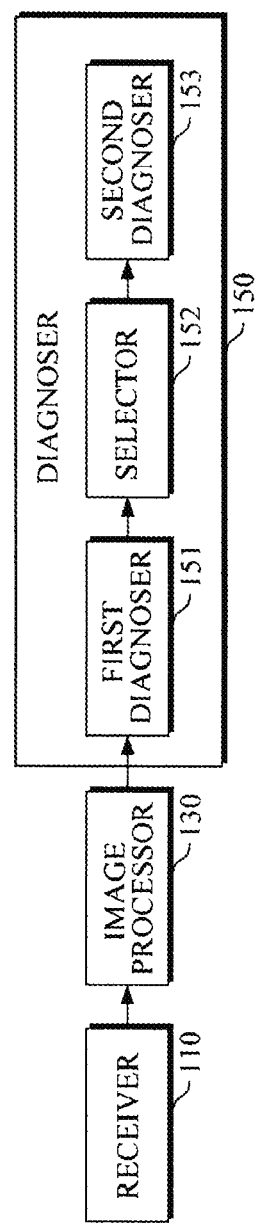
FIG. 3 is a configuration diagram illustrating a diagnoser, according to an embodiment.

Referring to FIG. 3, the diagnoser 150 may include a first diagnoser 151, a selection unit 152 and a second diagnoser 153. The first diagnoser 151 determines whether a lesion in each of a plurality of 2D slices generated by the image processor 130 is benign or malignant. For instance, the first diagnoser 151 segments a lesion such that a location of the lesion from each of the 2D slices is detected, and an accurate contour of the lesion is displayed based the detected location. For example, the first diagnoser 151 segments a lesion using various segmentation schemes including a region growing algorithm, a level set algorithm, and a genetic algorithm.

In addition, the first diagnoser 151 is configured to extract features of the segmented lesion to make a determination as to whether a particular segment of the lesion shown in each of the 2D slices is benign or malignant. The features of the segmented lesion are morphological features, such as contour shape, margin, direction, speculation, and micro-lobulation of a lesion. In another example, the features of the segmented lesion are the image's unique characteristics. In the case of an ultrasound image, features of a lesion may include an echo pattern and posterior acoustic shadow.

The first diagnoser 151 is configured to generate a feature vector using extracted features of a lesion and apply the feature vector to at least one diagnostic model to thereby classify a lesion as either benign or malignant. The first diagnoser 151 is also configured to calculate a confidence level of the classification result. In one illustrative example, the operation of generating a diagnostic model, the operation of classifying a lesion as either benign or malignant using a diagnostic model, and the operation of calculating a confidence level of the classification result are performed through machine learning. For example, various kinds of algorithms, including neural network, Bayesian classifier, multi-layer perceptron, and Support Vector Machine (SVM), may be utilized for machine learning.

In one illustrative configuration, a diagnostic model is generated as follows: features of a lesion in each 2D slice generated from previously acquired volume data sets are extracted; a feature vector is generated using the extracted features; the lesion is classified as either benign or malignant with respect to the feature vector; and results of the classification are used as training data for generating a diagnostic model.

The first diagnoser 151 is configured to diagnose each of the 2D slices generated by the image processor 130 using at least one diagnostic model.

In one example, in the case of liver, a cyst, or a hemangioma, a cross-section cutting direction does not make a big difference in the form of a lesion. Thus, even in the case where a diagnostic model, generated with reference to a specific cross-section cutting direction, is used to perform diagnosis on a 2D slice generated referencing a different cross-section cutting direction, it does not cause a significant difference to a diagnosis result. Accordingly, the first diagnoser 151 performs diagnosis by generating a single diagnostic model through machine learning using 2D slices, which are generated as training data by cutting previously acquired volume data from a predetermined cross-section cutting direction. The first diagnoser 151 then applies each of the generated 2D slices to the diagnostic model.

In another example, in the case of breast or lung, a lesion may have a different form in each 2D slice according to a cross-section cutting direction. Thus, a diagnosis result of a 2D slice may be dependent on a cross-section cutting direction. Accordingly, the first diagnoser 151 generates diagnostic models according to different cross-section cutting directions of 2D slices generated at the image processor 130. The first diagnoser 151 then perform diagnosis by applying the 2D slices to the diagnostic models, respectively.

For instance, the first diagnoser 151 generates diagnostic models using 2D slices as training data, which includes cross sections of previously-acquired volume data cut from different directions. Then, the first diagnoser 151 performs diagnosis on each of the 2D slices by applying the 2D slices to respective diagnostic models, which are generated based on cutting directions that are identical to those of the 2D slices.

Based on results of the determinations made by the first diagnoser 151 as to the 2D slices, the selector 152 selects some of the 2D slices. For instance, the selector 152 selects some of the 2D slices based on a classification result of a lesion in each of the 2D slices as either benign or malignant, based on a confidence level of the classification result, or based on both. At this point, the 2D slice is selected using various selection techniques, such as ranking-based selection, tournament selection, roulette wheel, and probability sampling.

Figure 7:
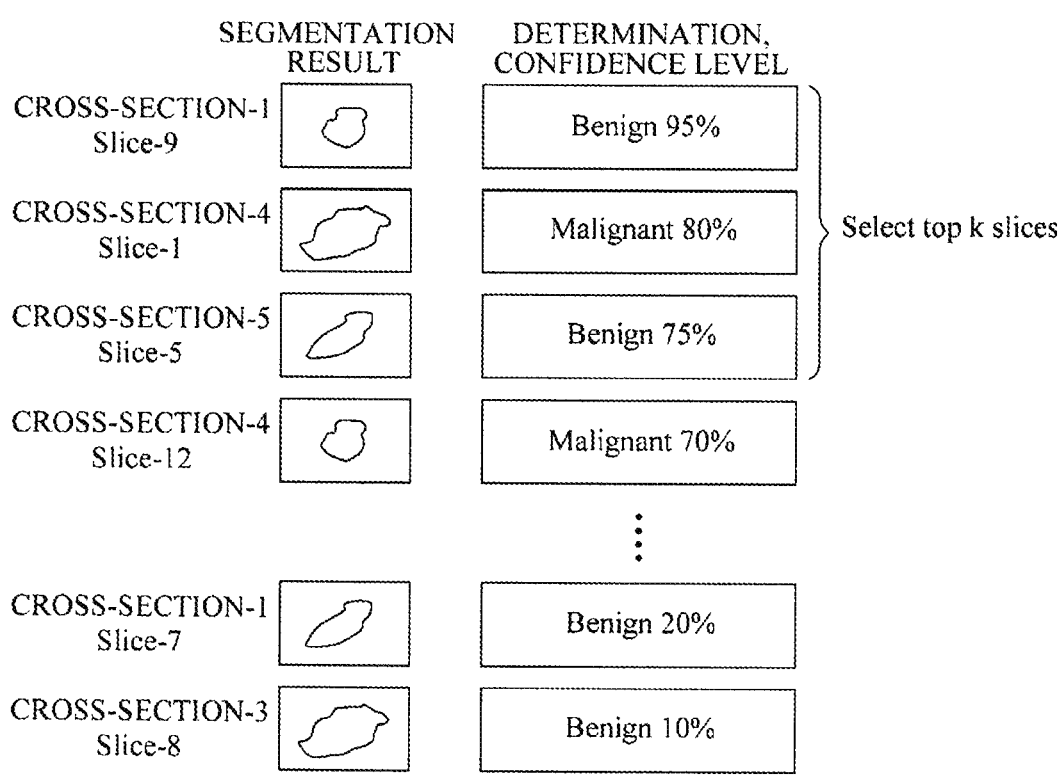
FIGS. 7 to 9 are examples of a method for selecting a two-dimensional (2D) slice.

Referring to FIG. 7, the selector 152 is configured to select k number of 2D slices in descending order of confidence levels thereof. In the example shown in FIG. 7, a specific numerical value (e.g., cross-sections 1, 3, 4, and 5) assigned to a cross section indicates that a specific cross-section is generated from a specific cutting direction. Slices 5, 7, 8, and 9 are classified as benign, and slices 1 and 12 are classified as malignant. The selector 152 aligns the 2D slices generated by the image processor 130 in descending order of confidence levels of classification results thereof, and selects k number of the 2D slices in descending order of the confidence levels.

Figure 8:
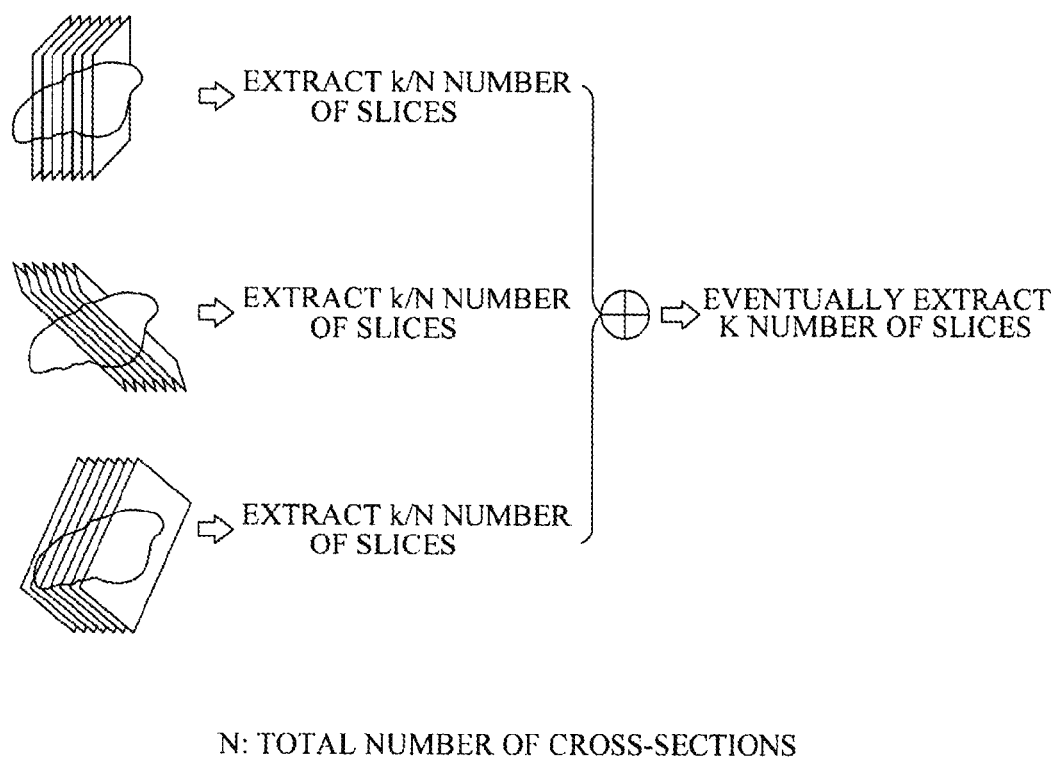

Referring to FIG. 8, the selector 152 is further configured to extract a predetermined number of 2D slices of volume data cut from different cross-section cutting directions, and select k number of 2D slices from the extracted 2D slices. In the example of FIG. 8, when N number of cross-section cutting directions is used to generate 2D slices, the selector 152 randomly selects k/N number of 2D slices with higher confidence levels to thereby select k number of 2D slices.

Figure 9:
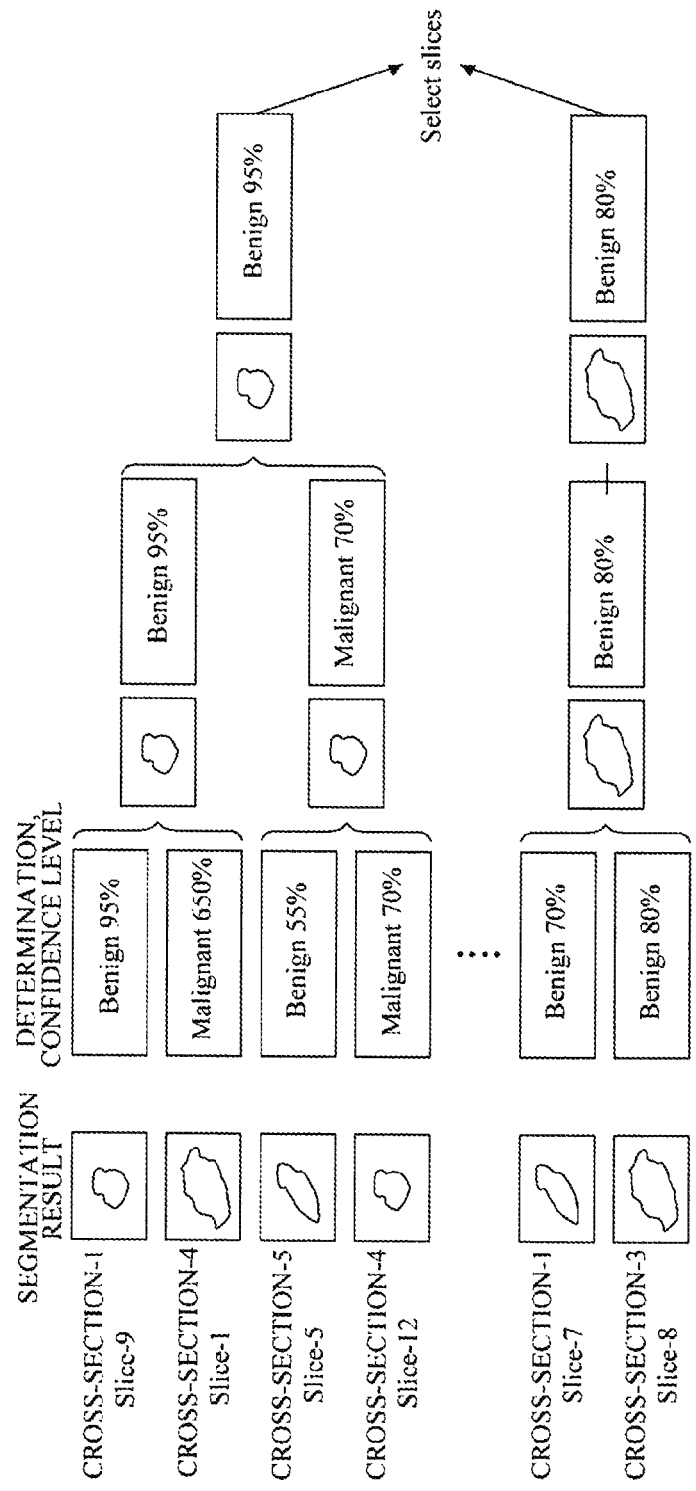

Referring to FIG. 9, the selector 152 binds two or more 2D slices into one group, compares confidence levels of the 2D slices in the group, and selects one or more 2D slices in descending order of the confidence levels thereof. The selector 142 also randomly binds the selected 2D slices into one group, compares confidence levels thereof, and selects one or more 2D slices in descending order of the confidence levels thereof. The selector 152 may repeat the above process until k number of 2D slices is selected.

The second diagnoser 153 is configured to make a final determination as to whether a lesion in each of the 2D slices is benign or malignant based on results of the determination relative to the k number of 2D slices selected by the selector 152. For instance, the second diagnoser 153 makes a final determination as to whether a lesion in each of the k number of 2D slices is benign or malignant using a voting method, which includes majority voting, a statistical method, which includes average, and an ensemble method which includes Adaboost, Bayes optimal classifier, and bootstrap aggregating.

In one example, in the case where two out of five 2D slices selected by the selector 152 are classified as malignant and other three 2D slices are classified as benign, the second diagnoser 153 makes a final determination that a lesion is benign.

In another example, in a case where two out of five 2D slices selected by the selector 152 are classified as malignant with confidence levels of 60% and 75%, respectively, while three other 2D slices are classified as benign with confidence levels of 60%, 80% and 85%, respectively, an average confidence level relative to malignancy is 67.5% and an average confidence level relative to benignity is 75%. Because a confidence level of benignity is greater than that of malignancy, the second diagnoser 153 makes a final determination that a lesion is benign.

Again, referring to FIG. 2, the diagnoser 150 selects one or more diagnostic models from diagnostic models, and determines benignity or malignancy of a lesion using an integrated diagnostic model, which is a combination of the selected diagnostic models, as contrary to the example shown in FIG. 3. For example, the diagnoser 150 integrates diagnostic models, each diagnostic model generated according to a different cross-section cutting direction, into one diagnostic model, and applies 2D slices generated by the image processor 130 to the integrated diagnostic model in order to deduct a final diagnosis result.

For example, the diagnoser 150 selects from diagnostic models one or more diagnostic models, which are generated based on cutting directions that are identical to those of the 2D slices generated at the image processor 130. The diagnoser 150 integrates the selected diagnostic models into one integrated diagnostic model. The diagnoser 150 generates a feature vector by calculating feature values of each of the 2D slices, and applies the feature vector to the integrated diagnostic model to determine whether a lesion in each of the 2D slices is benign or malignant.

The receiver 110, the image processor 130, the virtual plane generator 131, the slice generator 132, the diagnoser 150, the first and second diagnosers 151 and 153, and the selector 152 described herein may be implemented using hardware components. For example, controllers, generators, microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

Figure 10:
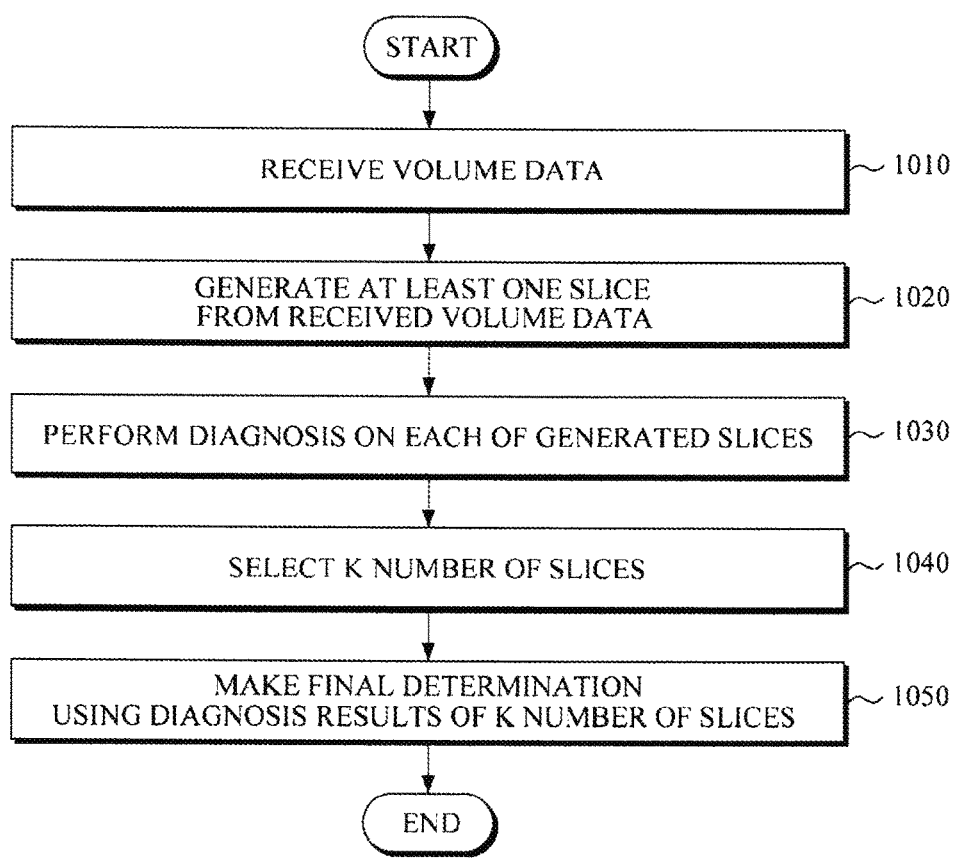
FIG. 10 is a flow chart for CAD, according to an embodiment.

FIG. 10 is a flow chart illustrating a method for CAD, according to an embodiment.

Referring to FIG. 10, at operation 1010, the method receives volume data through the receiver 110. At operation 1020, through the image processor 130, the method generates 2D slices including cross-sections of the received volume data cut by at least one cutting direction.

At operation 1030, using the diagnoser 150, the method determines whether a lesion in each of the 2D slices is benign or malignant. In one example, the method uses the diagnoser 150 to apply the 2D slices generated at operation 1020 to a single diagnostic model generated based on a particular cross-section cutting direction in order to classify a lesion in each of the 2D slices as either benign or malignant, and calculate a confidence level of the classification result.

In another example, the method uses the diagnoser 150 to apply each of the 2D slices, generated at operation 1020, to diagnostic models generated based on different cross-section cutting directions in order to classify a lesion in each of the 2D slices as either benign or malignant, and calculate a confidence level of the classification result. In one example, the method uses the diagnoser 150 to apply the plurality of 2D slices to respective diagnostic model which are generated based on cutting directions, which are identical to those of the 2D slices among the diagnostic models. At operation 1040, the method uses the diagnoser 150 to select some of the 2D slices based on results of the determinations thereof. At this point, the 2D slices may be selected using various selection techniques, such as ranking-based selection, tournament selection, roulette-wheel selection, and probability sampling.

When some of the 2D slices are selected, at operation 1050, the method uses the diagnoser 150 to make a final determination as to whether a lesion in each of the 2D slices is benign or malignant based on results of the determination relative to the selected 2D slices. The final determination may be made using a voting method including majority voting, a statistical method including average, and an ensemble method including Adaboost, Bayes optimal classifier, and bootstrap aggregating.

Figure 11:
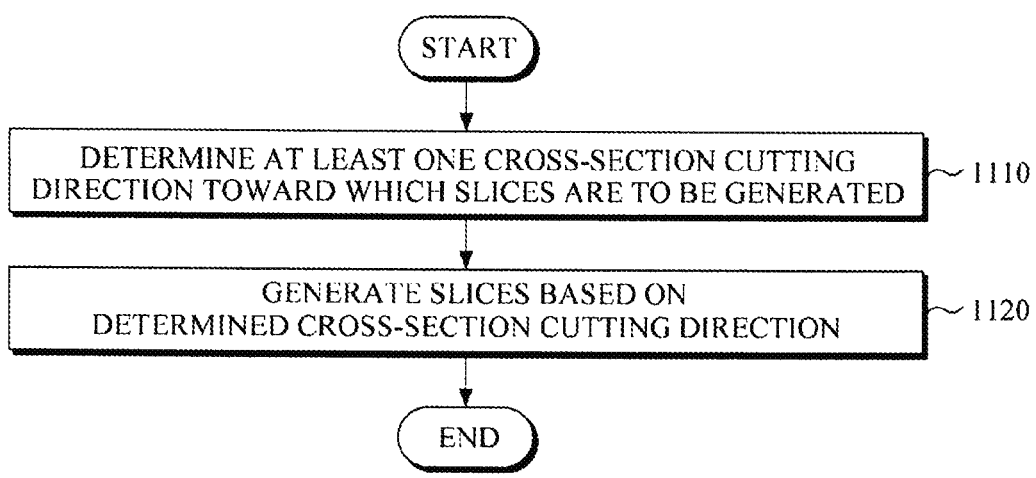
FIG. 11 is a flow chart illustrating a method for generating 2D slices from volume data, according to an embodiment.

FIG. 11 is a flow chart illustrating a method for generating 2D slices from volume data, according to an embodiment.

Referring to FIG. 11, at operation 1110, the method receives volume data from the receiver 110, and generates at least one virtual plane from the received volume data in 1110. The method generates at least one virtual plane by performing full search or PCA. For instance, the method determines at least one cross-section cutting direction toward which slices are to be generated. However, the present disclosure is not limited thereto, and other various methods may be applied. For example, the method may generate at least one virtual plane based on a user's input information.

In the case where at least one virtual plane is generated, at operation 1120, the method generates 2D slices including cross sections of volume data cut by the generated virtual plane. The method determines a cross-section cutting direction and generates 2D slices of the volume data cut based on the determined cross-section cutting direction.

Figure 12:
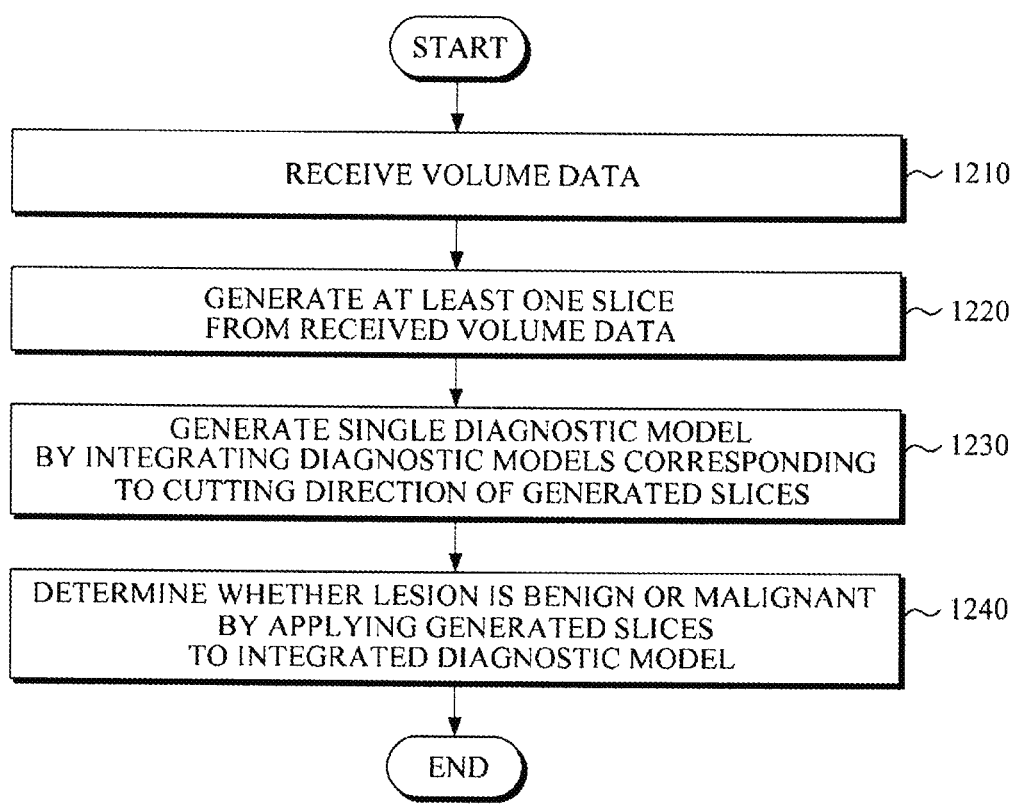
FIG. 12 is a flow chart illustrating a method for CAD, according to another embodiment.

FIG. 12 is a flow chart illustrating a method for CAD, according to another embodiment. Referring to FIG. 12, at operation 1210, the method receives volume data through the receiver 110. At operation 1220, the method uses the image processor 130 to generate 2D slices including cross-sections of the received volume data cut from at least one cross-section cutting direction. The 2D slices may be generated using the above-mentioned methods.

At operation 1230, the method uses the diagnoser 150 to generate an integrated diagnostic model by integrating diagnostic models corresponding to cross-section cutting directions of the 2D slices into one integrated diagnostic model. For instance, the method uses the diagnoser 150 to select one or more diagnostic models, which are generated based on cross-section cutting directions that are identical to those of the 2D slices. Then, the method generates an integrated diagnostic model by integrating the selected diagnostic models.

At operation 1240, the method uses the diagnoser 150 to apply the 2D slices to the integrated diagnostic model to make a determination as to whether a lesion in each of the 2D slices is benign or malignant.

It is to be understood that in the embodiment of the present invention, the operations in FIGS. 10-12 are performed in the sequence and manner as shown although the order of some operations and the like may be changed without departing from the spirit and scope of the described configurations. In accordance with an illustrative example, a computer program embodied on a non-transitory computer-readable medium may also be provided, encoding instructions to perform at least the method described in FIGS. 10-12.

Program instructions to perform a method described in FIGS. 10-12, or one or more operations thereof, may be recorded, stored, or fixed in one or more non-transitory computer-readable storage media. The program instructions may be implemented by a computer. For example, the computer may cause a processor to execute the program instructions. The media may include, alone or in combination with the program instructions, data files, data structures, and the like. Examples of non-transitory computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein may be easily construed by programmers skilled in the art to which the embodiments pertain based on and using the flow diagrams and block diagrams of the figures and their corresponding descriptions as provided herein.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method for medical diagnostics, comprising:
receiving three-dimensional (3D) volume data of at least a part of an object;
generating two-dimensional (2D) slices including cross-sections of the 3D volume data based on a cross-section cutting direction;
classifying a lesion in at least two of the generated 2D slices;
calculating confidence levels of results of the classification;
selecting a plurality of the at least two 2D slices based on the confidence levels of the results of the classification; and
classifying a lesion included in the 3D volume data based on at least one of the classification results of the selected 2D slices or the confidence levels of the classification results of the selected 2D slices.

2. The method of claim 1, further comprising:
outputting the classification result of the lesion included in the 3D volume data.

3. The method of claim 1, wherein the classifying of the lesion in at least two of the generated 2D slices comprises applying the at least two 2D slices to a diagnostic model to classify the lesion in the at least two 2D slices.

4. The method of claim 3, wherein the classifying of the lesion in at least two of the generated 2D slices comprises applying the at least two 2D slices to a single diagnostic model that is generated based on the cross-section cutting direction.

5. The method of claim 3, wherein the classifying of the lesion in at least two of the generated 2D slices comprises applying the at least two 2D slices to respective diagnostic models that are generated based on cross-section cutting directions of the at least two 2D slices.

6. The method of claim 1, wherein the generating of the 2D slices comprises:
generating at least one virtual plane; and
generating the 2D slices including cross-sections of the 3D volume data cut by the virtual plane.

7. The method of claim 6, wherein the generating of the at least one virtual plane comprises at least one of:
generating the at least one virtual plane by changing coefficient values of a plane equation that represents an arbitrary plane of the 3D volume data;
generating the at least one virtual plane by performing principal component analysis (PCA) on the 3D volume data; or
generating the at least one virtual plane based on a user's input information.

8. The method of claim 7, wherein the generating of the at least one virtual plane further comprises at least one of:
determining feature points having a predetermined feature from among voxels of the 3D volume data based on values of the voxels, and generating the at least one virtual plane based on a distribution of the feature points by performing the PCA;
calculating a first principal component vector corresponding to an axis in a direction in which a change in the 3D volume data is the greatest by performing the PCA, and generating the at least one virtual plane with reference to the first principal component vector; or
detecting a mass included in the 3D volume data based on values of voxels of the 3D volume data, and generating the at least one virtual plane based on a distribution of points included in the mass by performing the PCA.

9. An apparatus for medical diagnostics, comprising:

a receiver configured to receive three-dimensional (3D) volume data of at least a part of an object; and at least one processor configured to:
generate two-dimensional (2D) slices including cross-sections of the 3D volume data based on a cross-section cutting direction,
classify a lesion in at least two of the generated 2D slices,
calculate confidence levels of the results of the classification,
select a plurality of the at least two 2D slices based on the confidence levels of the results of the classification, and
classify a lesion included in the 3D volume data based on at least one of the classification results of the selected 2D slices or the confidence levels of the classification results of the selected 2D slices.

10. The apparatus of claim 9, wherein the at least one processor is further configured to output the classification result of the lesion included in the 3D volume data.

11. The apparatus of claim 9, wherein the at least one processor is further configured to classify the lesion in the at least two 2D slices by applying the at least two 2D slices to a diagnostic model.

12. The apparatus of claim 11, wherein the at least one processor is further configured to classify the lesion in the at least two 2D slices by applying the at least two 2D slices to a single diagnostic model generated based on a cross-section cutting direction.

13. The apparatus of claim 11, wherein the at least one processor is further configured to classify the lesion in the at least two 2D slices by applying the at least two 2D slices to respective diagnostic models generated based on cross-section cutting directions of the at least two 2D slices.

14. The apparatus of claim 9, wherein the at least one processor is further configured to:
generate at least one virtual plane, and
generate 2D slices of cross-sections of the 3D volume data cut by the virtual plane.

15. The apparatus of claim 14, wherein the at least one processor is further configured to generate the at least one virtual plane by changing coefficients of a plane equation of an arbitrary plane of the 3D volume data by at least one of:
performing principal component analysis (PCA) on the 3D volume data, or
based on a user's input information.

16. The apparatus of claim 15, wherein the at least one processor is further configured to:
determine feature points with a predetermined feature from among voxels of the 3D volume data based on values of the voxels, and generate the at least one virtual plane based on a distribution of the feature points,
calculate a first principal component vector corresponding to an axis in a direction toward which a greatest change occurs in the 3D volume data by performing the PCA, and generate the at least one virtual plane based on the first principal component vector, or
detect a mass included in the 3D volume data based on values of voxels of the 3D volume data, and generate the at least one virtual plane based on a distribution of points included in the mass by performing the PCA.

17. The apparatus of claim 9, wherein the at least one processor is further configured to:
generate a feature vector using extracted features of the lesion in the at least two 2D slices, and
apply the feature vector to a diagnostic model to classify the lesion in the at least two 2D slices.

18. The apparatus of claim 9, wherein the at least one processor is further configured to:
bind two or more 2D slices into one group,
compare confidence levels of the 2D slices in the group, and
select one or more 2D slices in descending order of the confidence levels thereof.

19. The apparatus of claim 9, wherein the at least one processor is further configured to:
randomly bind the selected 2D slices into one group,
compare confidence levels thereof, and
select one or more 2D slices in descending order of the confidence levels thereof.

20. A computer program product comprising a non-transitory computer readable storage medium having a computer readable program stored therein, wherein the computer readable program, when executed on at least one processor, configures the at least one processor to:
receive three-dimensional (3D) volume data of at least a part of an object;
generate two-dimensional (2D) slices including cross-sections of the 3D volume data based on a cross-section cutting direction;
classify a lesion in at least two of the generated 2D slices;
calculate confidence levels of results of the classification;
select a plurality of the at least two 2D slices based on the confidence levels of the results of the classification; and
classify a lesion included in the 3D volume data based on at least one of the classification results of the selected 2D slices or the confidence levels of the classification results of the selected 2D slices.

* * * * *